United States Patent
Parekh et al.

(10) Patent No.: US 6,649,153 B1
(45) Date of Patent: Nov. 18, 2003

(54) SKIN FRIENDLY ANTIPERSPIRANT COMPOSITION AND METHOD OF MAKING

(75) Inventors: Jawahar C. Parekh, Livingston, NJ (US); Zijun Li, Westfield, NJ (US)

(73) Assignee: Reheis Inc., Berkley Heights, NJ (US)

( * ) Notice: Subject to any disclaimer, the term of this patent is extended or adjusted under 35 U.S.C. 154(b) by 0 days.

(21) Appl. No.: 10/244,701

(22) Filed: Sep. 16, 2002

(51) Int. Cl.$^7$ ............... A61K 7/32; A61K 7/34; A61K 7/38; A61K 7/00
(52) U.S. Cl. ............... 424/65; 424/66; 424/68; 424/400; 424/401
(58) Field of Search ............... 424/65, 66, 68, 424/400, 401

(56) References Cited

U.S. PATENT DOCUMENTS

| | | |
|---|---|---|
| 3,359,169 A | 12/1967 | Slater et al. |
| 3,405,153 A | 10/1968 | Jones et al. |
| 3,420,932 A | 1/1969 | Jones et al. |
| 3,532,130 A | 10/1970 | Jones et al. |
| 3,873,686 A | 3/1975 | Beekman |
| 3,981,986 A | 9/1976 | Rubino |
| 4,829,092 A | 5/1989 | Nelson et al. |
| 5,043,359 A | 8/1991 | Ward et al. |
| 5,215,759 A | 6/1993 | Mausner |
| 5,409,691 A | 4/1995 | Swain |
| 5,871,754 A | 2/1999 | Briggs et al. |
| 5,939,057 A | 8/1999 | Provancal et al. |
| 5,972,362 A | 10/1999 | Wenker |
| 6,066,314 A | 5/2000 | Tang et al. |
| 6,403,072 B1 | 6/2002 | Scavone |

FOREIGN PATENT DOCUMENTS

| | | |
|---|---|---|
| EP | 0 194 097 | 10/1986 |
| EP | 0 512 770 | 11/1992 |
| EP | 0 661 963 | 7/1995 |
| EP | 0 789 554 | 8/1997 |
| EP | 0 812 182 | 12/1997 |
| WO | WO 91/11171 | 8/1991 |
| WO | WO 97/07779 | 3/1997 |

Primary Examiner—Shelley A. Dodson
(74) Attorney, Agent, or Firm—Arthur J. Plantamura

(57) ABSTRACT

An improved skin friendly antiperspirant is provided in which a suitable polyhydric alcohol e.g., glycerin, is complexed with the antiperspirant of the type of activated or nonactivated aluminum or aluminum/zirconium salt that are commonly considered antiperspirant active materials and are covered by FDA OTC Tentative Final Monograph as Category I. Suitable antiperspirant salts include (but are not limited to): aluminum chlorohydrate, aluminum sesquichlorohydrate, aluminum chlorohydrex PG, aluminum dichlorohydrex PG, aluminum sesquichlorohydrex PG, aluminum chlorohydrex PEG, aluminum sesquichlorohydrex PEG, aluminum chloride (15 percent or less aqueous solutions), aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum zirconium trichlorohydrex Gly, aluminum zirconium penta chlorohydrex Gly, aluminum zirconium tetrachlorohydrex Gly, aluminum zirconium octachlorohydrex Gly, buffered aluminum sulfate, basic aluminum chlorides, zirconium hydroxychloride, zirconyl chloride, basic aluminum nitrates, basic aluminum chlorides combined with zirconyl oxychloride and/or hydroxychloride and organic complexes of each of basic aluminum chlorides with or without zirconyl chloride or zirconium hydroxychloride and mixture of any of the foregoing. Aluminum, zinc or zinc and zirconium complexes or aluminum, zinc and zirconium complexes with having metals/anion ratio of 0.9:1 to 2:1 where the anion is Cl, Br, I and/or NO, with or without additives such as amino acids or polyhydric alcohols.

36 Claims, No Drawings

SKIN FRIENDLY ANTIPERSPIRANT COMPOSITION AND METHOD OF MAKING

BACKGROUND OF THE INVENTION

The invention relates to a novel skin friendly antiperspirant composition in which the modifying component comprises a polyhydric alcohol, preferably glycerin, is substantially complexed within the antiperspirant. The invention is applicable to the types of activated or nonactivated aluminum or aluminum/zirconium salts that are commonly considered antiperspirant active materials and are covered by FDA OTC Tentative Final Monograph as Category I.

It is desirable for an antiperspirant product to provide aesthetics (pleasing skin feel) in addition to excellent antiperspirancy. Appearance and feel of the skin is a major concern to the consumer as well as to the cosmetic industry. In order to understand how to control skin feel and appearance it is necessary to gain a better understanding of biological/biophysical factors affecting stratum corneum (SC), the outermost layer of the skin.

The structure and function of the stratum corneum has been the subject of intensive investigation over the past three decades. Its structure in the published literature of L. D. Rheim, etal, "Development of Stratum Corneum Lipid Model to Study the Cutaneous Moisture Barrier Properties" Colloids and Surfaces, 48 (1990) 1–11 Elseiver Science Publishers, has been likened to brick wall, with the bricks representing corneocytes themselves and the 'mortar' representing the highly specialized intercellular lipids. The intercellular lipids are composed primarily of ceramides, cholesterol and fatty acids together with smaller amounts of phospholipids and glucosylceramides. These lipids form the major permeability barrier to the loss of water from the underlying epidermis and also from the part of the intercellular cement which helps to maintain the integrity of the tissue.

Human stratum corneum contains 15 such corneocyte/lipid layers. The corneocytes contain mainly the structural protein keratin.

A major function of the stratum corneum is to provide a barrier to evaporation of water. If this layer is removed from the skin e.g., by tape stripping, a fifty (50) fold increase in the rate of water loss ensues. Moisturization capacity of the SC is a major concern to the cosmetic industry since consumers are highly concerned about dry skin and moisture replenishment. Additionally dry skin can result in increased incidence of cuts during shaving.

The intercellular lipids are thought to play a major role in preventing water loss through the stratum corneum. To better understand the barrier function of the intercellular lipids and their role in regulating moisture loss from skin, numerous researchers are probing the structural organization of stratum corneum lipids and trying to understand what is the mechanism through which polyols and especially glycerin, mediate its effect on alleviating skin xerosis in vivo.

It has been shown that glycerin does not exhibit humectant properties at or below 6% RH (relative humidity) that is, neat glycerin samples exposed to 6% RH did not gain water over time. Thus, in low relative humidity climates it is unlikely that glycerin improves dry skin by humectancy. Rheim, et al. found that by incorporating glycerin into lipid model (at 10% levels) it prevented the formation of solid crystals and maintained a largely liquid crystalline state for the lipid/glycerin system. It was therefore concluded that in dry atmosphere glycerin may act as a moisturizer by inhibiting the lipid phase transitions from liquid to solid crystals. Maintaining the lipid in a liquid crystalline state with only small amounts of solid crystals may be the key for optimal barrier function.

Using in vitro stratum corneum extensibility model, Rawling, et al ("The effect of glycerol and humidity on desmosome degradation in stratum corneum", Arch. Dermatol Res. 1995 287: 437–464) have consistently found glycerin to be superior to all other humectants and polyols in skin xerosis and their effect of inhibiting lipid crystallinity.

It has also been reported that enzymatic activity, and thereby desmosome degradation occurs only above a certain water content in the stratum corneum. When the stratum corneum lipid structure is disturbed, the resulting reduction in stratum corneum hydration leads to the retention of corneocytes on the skin's surface and the manifestation of skin xerosis due to reduced desmosome degradation. If, therefore, stratum corneum moisturization and water barrier function can be restarted by the topical use of a suitable moisturizer, the desquamatory process can be restored by the topical use of an ideal moisturizer and xeratic skin conditions may be treated more effectively. One compound that meets all these requirements is glycerin. The action of glycerin has been explained in terms of its occlusive, humectant and lipid phase modulating properties, all of which translate into moisturization and barrier improvements for the stratum corneum. More recently, it has been shown that glycerin aids enzyme layers of desmosomes in the stratum corneum. All of this represents an alternate, more likely molecular mechanism of action for skin moisturizing by glycerin.

Glycerin is not the only material that has been shown to condition the skin without hydrating it. The effects of another nonhygroscopic skin softener, a modified triglyceride known as glyceridacid was reported by R. S. Summers, et al, "The effect of lipids, with and without humectant, on skin xerosis. J. Soc. Cosmetic Chemist Vol. 47; 27–39", as exerting skin softening effects via interaction with the stratum corneum lipids. Recently another class of compounds known as α hydroxyacids have been investigated and these compounds which, are non humectants have been found to plasticize the stratum corneum even under conditions of low relative humidity (20% RH). Fraebe, et al, "Prevention of Stratum Corneum lipid phase transitions in vitro by glycerol—an alternative mechanism for skin moisturization". J. Mattai, J. Soc. Cosmetic Chemist Vol. 41, 51–65 reported that α hydroxy acids, particularly the longer chains ($C_{10}$, $C_{12}$) species may enable these compounds to penetrate the fatty acid chains of the bilayer, interrupting the close packing of these chains and thereby enhancing the fluidity of the membrane.

As pointed out by P. Thau ("Glycerin Current Insights into the Functional Properties of Classic Cosmetic Raw Material", J. Cosmetic Sci. Vol. 53, 229–236") studies conducted within the past twenty to twenty five years have enabled us to gain significant understanding of the complex interactions of glycerin with the epidermis. Results of these studies in the form of interaction of glycerin with the epidermis are listed below.

1. increases the extensibility of the stratum corneum
2. increases the water gradient in the skin
3. reduces surface roughness (may not be caused solely by moisturization)
4. penetrates into the phospholipid bilayers
5. maintains the intercellular lipid cement in a fluid liquid crystal state, particularly under conditions of low temperature and low RH 6. accelerates recovery of barrier function in vivo
7. serves to accelerate wound healing
8. aids in the digestion of desmosomes
9. provides a skin protection function
10. enhances corneocyte desquamation
11. does not interfere with biochemical processes in the skin The preservation of skin structure and function with concomittant mildness and metabolic inactivity truly makes glycerin the quintessential cosmetic ingredient. However, blending of glycerin with antiperspirant powder (basic aluminum halides, nitrate, or aluminum/zirconium complexes as identified in OTC monograph) in a typical antiperspirant stick formulation results in agglomeration and formation of gritty particles requiring use of flow enhancers such as silica and talc. In general, colloidal silica in amounts up to about 1% by weight by the total composition and preferably about 0.05 to 0.5% is used. However, silica and talc present dusting and health related problems and the finished product does not provide excellent skin feel as they tend to increase drag.

Besides health concerns in handling of silica and talc, the products also affect aesthetics of the finished stick; the product tends to have grittiness and leaves moderate white residue on the skin.

Therefore, it is an object of this invention to provide an antiperspirant active composition which when formulated into an antiperspirant stick has an improved combination of functional properties, including excellent antiperspirancy, skin conditioning and moisturizing.

It is another objective of this invention to provide an active which does not require the use of silica and talc as flow enhancers in the final formulation thus simplifying the formulation and manufacturing process.

It is yet another objective of this invention to provide an active which provides excellent skin feel (i.e., no grittiness).

It is yet another objective of this invention to maintain high antiperspirancy for the new product.

It is yet another objective of this invention to define the morphological parameters of the active powder which gives the desired properties.

It is yet another objective of this invention to provide improved color (whiteness) of the product.

SUMMARY OF THE INVENTION

The novel skin friendly antiperspirant of the invention in which a suitable polyhydric alcohol, e.g., glycerin, is complexed with the antiperspirant is formed with the type of activated or nonactivated aluminum or aluminum/zirconium salts that are commonly considered antiperspirant active materials and are covered by FDA OTC Tentative Final Monograph as Category I. Suitable antiperspirant salts include (but are not limited to): aluminum chlorohydrate, aluminum sesquichlorohydrate, aluminum chlorohydrex PG, aluminum dichlroohydrex PG, aluminum sesquichlorohydrex PG, aluminum chlorohydrex PEG, aluminum sesquichlorohydrex PEG, aluminum chloride (15 perecent or less aqueous solutions), aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum zirconium trichlorohydrex Glycine (Gly), aluminum zirconium penta chlorohydrex Gly, aluminum zirconium tetrachlorohydrex Gly, aluminum zirconium octachlorohydrex Gly, buffered aluminum sulfate, basic aluminum chlorides, zirconium hydroxychloride, zirconyl chloride, basic aluminum nitrates, basic aluminum chlorides combined with zirconyl oxychloride and/or hydroxychloride and organic complexes of each of basic aluminum chlorides with or without zirconyl chloride or zirconium hydroxychloride and mixture of any of the foregoing. Aluminum or aluminum and zirconium complexes having metals/anion ratio of 0.9:1 to 2.1:1 where an anion could be Cl, Br, I and/or $NO_3$, with or without additives such as amino acids or polyhydric alcohols.

A particular group of such antiperspirant active includes various aluminum-zirconium-glycine salts with the formula:

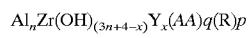

$$Al_nZr(OH)_{(3n+4-x)}Y_x(AA)q(R)p$$

wherein "n" is from 2.0 to 10.0; preferably from 3 to 8;
wherein "x" is from 1.4 to 12.3, calculated from metal to chloride ratio (M/Cl, 0.9:1–2.1:1); preferably from 2 to 8, wherein "Y" is Cl, Br, I and/or $NO_3$;
wherein "q" is from 0.5 to 3.0, preferably from 1 to 2; and AA is an amino acid, and wherein "R" is an organic solvent having at least two carbon atoms and at least one hydroxy group and "p" has a value of from zero to 1.5 and basic aluminum chlorides with the formula:

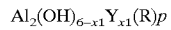

$$Al_2(OH)_{6-x1}Y_{x1}(R)p$$

wherein Y is Cl, Br, I and/or $NO_3$ and $x_1$ is greater than zero and less than or equal to six (i.e. $0 < x_1 \leq 6$).

The invention contemplates also those antiperspirant actives comprising aluminum and aluminum zirconium salts combined with zinc and/or tin, i.e. Al/Zr/Zn, Al/Zn, Al/Sn, Al/Zr/Sn, and the like,actives.

The polyhydric alcohol, which may be employed in preparing the skin friendly antiperspirant formulation of the invention may be selected from any of the suitable polyhydric and non-polyhydric alcohols which are generally used in cosmetic compositions and which are liquid at room temperature. These typically include liquid polyhydric alcohols having from 3 to 12 carbon atoms and three or more hydroxy groups such as, for example, glycerin, diglycerol, sorbitol, 1,2,4-butanetriol; 1,2,6-hexanetriol, etc. and mixtures thereof. Most preferred are glycerol and diglycerol. Nonpolyhydric alcohol compounds that may be used are glycol ether such as monoalkyl ethers or α hydroxy acids.

The primary aspect of the present invention is to provide an antiperspirant product that not only performs as a highly efficacious antiperspirant but further serves as moisturizer and plasticizer and minimizes skin irritation especially for people with sensitive skin. An ideal antiperspirant with these desirable features should minimize sweat secretion causing little or no irritation and without overdrying the skin or leaving it taut after sustained use of antiperspirant or dry deodorants.

DETAILED DESCRIPTION OF THE INVENTION

In accordance with the method of present invention an aqueous basic aluminum chloride solution or an aqueous basic aluminum chloride solution with an organic solvent such as propylene glycol, dipropylene glycol, tripropylene glycol, and the like as represented by the general formula:

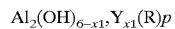

$$Al_2(OH)_{6-x1},Y_{x1}(R)p$$

wherein Y is Cl, Br, I and/or $NO_3$ and $x_1$ is greater than zero and less than or equal to six (i.e. $0 < x_1 \leq 6$) wherein "R" is an organic solvent having at least two carbon atoms and at least one hydroxy group and "p" has a value of from zero to 1.5, is mixed with glycerin at room temperature to about 105° C., may be refluxed for 30 minutes to about 4 hrs.; is cooled to room temperature and mixed with zirconium hydroxy chloride glycinate solution having Cl/Zr atomic ratio of (0.8:1 to 2:1) and which has been refluxed to 2 hrs. The resultant solution is allowed to react at least for 30 minutes and is then filtered to obtain slightly amber to colorless solution. This solution is then dried by a suitable conventional means (viz spray dryer, vacuum dryer, oven dryer, tray dryer, freeze dryer, etc.) to yield a homogeneous skin friendly composition having the desired characteristics.

In the method of the present invention, glycerin may be added to zirconium hydroxy glycinate solution before, during or after the refluxing step or it may be added after zirconium hydroxy glycinate solution has been added to basic aluminum chloride and just before the spray drying at room temperature or at temperature up to 100° C. Alternatively some of the glycerin may be added to basic aluminum chloride and the remainder to zirconium hydroxy glycinate solution.

The antiperspirant product of the invention comprises a novel complex composition in which part of the contained polyhydric alcohol, for example, glycerin, is complexed with the aluminum zirconium antiperspirant. It is postulated that approximately 20% to 70% of the glycerin is coordinated for aluminum zirconium antiperspirant complexes having Al/Zr atomic ratio of 2 to 10 and metals/anion ratio of 0.8 to 2.1:1; for basic aluminum chloride it appears to be less than 2% and the rest of the glycerin exists as a "free" glycerin. The amount of glycerin present as complexed depends upon the type of antiperspirant active, total concentration of glycerin and at what step of the reaction process it is added. Free glycerin means it can be titrated quantitatively by the standard analytical method. However, some evidence demonstrates that at least part of this "free" glycerin is absorbed and held at the surface of the complex. The combination of the presence of coordinated glycerin plus the presence of free glycerin appears to offer unique properties when formulated into an antiperspirant stick form and applied to human skin.

The coordination of glycerin molecule with aluminum-zirconium antiperspirant is demonstrated firstly by the chemical shift change ($^1$H NMR) and the broadening of the chemical shift of the glycerin peak(s); and secondly by the titration of the glycerin molecule in the aluminum-zirconium-glycerin antiperspirant.

A new broad signal at ~3.7 ppm was observed when $^1$H NMR was run on the aluminum-zirconium-glycerin antiperspirant, which is different from the three sharp multiple signals demonstrated by the glycerin molecule. This is an indication of the formation of a new interaction between the antiperspirant active and the glycerin molecule. Further, it has been discovered by the present invention that the complexation occurs between zirconium and glycerin.

In order to determine whether the polyhydric alcohol is complexed with aluminum to provide the composition of the invention or is not complexed, comparative experiments were run in which basic aluminum chloride solution (Reach 301, a product of Reheis Inc) was refluxed with glycerin for 4 hrs. and spray dried. The resultant powder was analyzed and the glycerin value that was titrated quantitatively by the standard analytical method was compared against the glyc erin value determined based on the total carbon analysis. Results are shown below.

| Example | Al | % Cl | Presence of % Glycerin Determined by Analytical Method | Presence of % Glycerin by Total Carbon Analysis |
| --- | --- | --- | --- | --- |
| 1 | 23.1 | 18.1 | 7.91 | 7.77 |

While not being bound by any theories it appears that if any glycerin is complexed with basic aluminum chloride it is appreciably less than the amount of glycerin complexed with an aluminum zirconium salt.

When chemical analysis was performed to calculate the glycerin value in aluminum-zirconium-glycerin antiperspirant, zirconium was first precipitated out because of the interference. Glycerin was found to be present in the zirconium precipitates. Further, it has been found that the value of glycerin by analytical titration is always less than the glycerin value calculated from total carbon analysis. The difference has been found to be the function of the type of antiperspirant, glycerin concentration and the process employed for making the product. The results indicate that glycerin is coordinated with the zirconium metal in the antiperspirant. Further there is less than 2% difference in the glycerin values in the aluminum-glycerin antiperspirant between chemical analysis by titration method and based on total analysis, providing additional indication that most of the glycerin is coordinated with zirconium. Also, $^1$H NMR of aluminum zirconium antiperspirant indicate chemical shift change and the broadening of the glycerin peaks due to complexation.

The antiperspirant salts which may be employed in preparing the novel complex of the invention include (but are not limited to) the following five groups:

A first group of such antiperspirant actives materials includes aluminum chlorohydrate, aluminum dichlorohydrate, aluminum sesquichlorohydrate, aluminum zirconium trichlorohydrate, aluminum zirconium tetrachlorohydrate, aluminum zirconium pentachlorohydrate, aluminum zirconium octachlorohydrate, aluminum zirconium trichlorohydrex glycine (gly), aluminum zirconium tetrachlorohydrex gly, and aluminum zirconium pentachlorohydrex gly and aluminum zirconium octachlorohydrex gly.

A second particular group of such antiperspirant actives include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrx gly, aluminum zirconium octachlorohydrex gly), aluminum chlorohydrex PG, aluminum chlorohydrex PEG, aluminum dichlorohydrex PG, and aluminum dichlorohydrex PEG. Aluminum zirconium trichlorohydrex PG, aluminum zirconium tetrachlorohydrex PG complex, etc. Aluminum zirconium complexes having Al/Zr atomic ratio of 2:1 to 10:1 and metals to anion ratio of 0.9:1 to 2.1:1 and organic complexes thereof.

A third group of such antiperspirant include basic aluminum chlorides represented by the formula $Al_2(OH)_{6-x1}Y_{x1}$ [wherein Y is Cl, Br, I and/or $NO_3$ and $0<x_1 \leq 6$] with or without zirconyl oxychlorides and hydroxy chlorides and mixtures of any of the foregoing.

A fourth particular group of such antiperspirant actives include the enhanced efficacy aluminum salts and the enhanced efficacy aluminum/zirconium salt-glycine materials, having enhanced efficacy due to improved molecular distribution, known in the art and discussed, for example in U.S. Pat. Nos. 4,359,456, 4,775,528, 5,718,876, 5,908,616 and EP Patents 0,191,628, 0,256,832.

A fifth group of such antiperspirant actives includes salts of aluminum and tin, or tin zirconium and aluminum or aluminum, zinc and zirconium, with or without such additives as amino acids or polyhydric alcohols and combinations thereof.

The process of the invention used in preparing the improved composition will become more readily apparent from the various illustrative but not limiting to examples which follow:

EXAMPLE 2

1700 g of Basic Aluminum Chloride (Reach 301, a product of Reheis Inc.) solution (11.9% Al, 9.5% Cl) was mixed with 125 g of glycerin. The mixture was placed in a conical flask with a reflux condenser. The solution was refluxed for 4 hours and was cooled to Rr. 1390 g of zirconium hydroxy chloride (ZHC) glycinate solution (13.5% Zr, 5.9% Cl, 11.2% glycine; ZHC solution was refluxed with glycine for 2 hours) was slowly added to the above RE301/glycerin solution at room temperature. The final solution was spray dried to yield a white powder which was micronized to obtain the desired particle size distribution.

EXAMPLES 3–7

The procedure of Example 2 was followed but the quantities of compounds used were increased to pilot plant level. Examples 3 to 7 in Table I illustrate the effect of spray drying conditions. Inlet temperature was varied from 450–600° F.; outlet temperature was in the range of 235±5° F. and different atomizers were used including CSE, porous metal, two fluid nozzle, MMDH, etc. to completely characterize the powder's physical and chemical properties.

All the samples, the results of which are set forth in Table I, were analyzed for complete chemical analysis, particle size, BET surface area as well as, total mercury intrusion volume, total pore area and average pore diameter. Particle size was measured using Microtrack Model No. SRA150 and porosity data was obtained using Micromeritics Autopore Mercury Porosimeter Model No. 9520. BET surface area was obtained using single point BET instrument manufactured by Quanta Chrome Corporation.

To characterize morphology of the powder the novel product was analyzed using: atomic force microscopy, single point BET surface area, mercury porosimeter, air classification of powder into coarse, fine and superfine fractions which were analyzed for surface area and particle size. Samples were also analyzed for surface energy to determine the cohesion energy as cohesion energy affects surface roughness.

In order to study the effect of glycerin on the morphology of the novel product of this invention, four samples of aluminum zirconium tetrachlorohydrex/ glycerin powder were prepared using the procedure of Example 2 but glycerin level was varied from about 2% to 17%. Chemical analysis of the samples is shown by Table II.

TABLE II

| Example | % Al | % Zr | % Cl | % glycine | % glycerin* |
|---|---|---|---|---|---|
| 8 | 15 | 13.2 | 17.5 | 11.4 | 1.86 |
| 9 | 13.48 | 14.06 | 17.57 | 11.67 | 3.79 |
| 10 | 14 | 13.1 | 17.4 | 10 | 7.83 |
| 11 | 12.2 | 12.3 | 15.6 | 10.6 | 17 |

*(glycerin is measured by analytical titration)

*(glycerin is measured by analytical titration)

Aluminum zirconium tetrachlorohydrex/glycerin powder samples of Table II were suspended in isopropanol, sonicated and then placed over freshly fractured mica discs. The advantage of freshly fractured mica discs is the complete flatness of their surfaces that allows a better recognition of thin or small particles relative to the underlying surface. The samples were allowed to dry in a closed petri dish then placed in freeze dryer for 24 hours (without freezing the samples) to remove most of the moisture from the particle surface to prevent it from interfering with the microscope tips. After 24 hours, samples were immediately placed in the microscope which was placed in a special glove box which was flooded with nitrogen gas in order to avoid fast adsorption of moisture on the particle's surface and the sample was scanned as soon as possible.

The atomic force microscopy (AFM) was used to obtain qualitative information on the surface changes due to the addition of glycerin.

Based on this study it appears that within the range of glycerin levels tested surface roughness of the particle decreases as the amount of glycerin is increased.

A relatively great proportion of the atoms of a fine powder are in or near the surface. If, in addition, the powder particles have pores within their structure, the proportion of the exposed atom is still greater. This causes powder to exhibit distinctly different properties and it is strongly dependent on the magnitude of their surface areas and the nature of their porosity. The influence is so pronounced in some instances that surface area and structure appear almost as important as chemical composition. For this reason, powders were analyzed using mercury porosimeter to characterize the pore size distribution, pore diameter, pore volume and surface area was determined using BET surface area measurement.

TABLE I

| Example | % Al | % Zr | % Cl | % glycine | % glycerin* | % particle <10μ | LOD (105° C./2 hrs) | BET (m2/gm) | Bulk Density (gm/cc) | Total Intrusion Volume (ml/gm) | Total Pore Area (m2/gm) | % porosity |
|---|---|---|---|---|---|---|---|---|---|---|---|---|
| 2 | 13.56 | 12.95 | 15.93 | 11.30 | 7.42 | 100.0 | 10.2 | 1.81 | 0.56 | — | — | — |
| 3 | 14.00 | 13.10 | 17.4 | 10.00 | 7.83 | 98.9 | 6.76 | 2.16 | 0.66 | 0.785 | 10.57 | 61.19 |
| 4 | 13.84 | 12.95 | 17.2 | 9.88 | 7.74 | 99.8 | 7.68 | 2.50 | 0.59 | 0.6753 | 6.284 | 57.14 |
| 5 | 13.56 | 12.70 | 16.86 | 9.66 | 7.59 | 98.2 | 8.10 | 2.99 | 0.56 | 0.6075 | 7.075 | 54.62 |
| 6 | 13.73 | 12.85 | 17.07 | 9.81 | 7.68 | 100.0 | 8.32 | 2.99 | 0.68 | 0.4354 | 1.475 | 37.29 |
| 7 | 13.65 | 12.77 | 17.0 | 9.75 | 7.63 | 2.9 | 6.65 | 0.23 | 1.08 | 0.438 | 0.227 | 45.65 |

Pores may have a continuous path from one side to the other and such products are generally recognized as porous. Passageways completed through are not a necessary criterion, however, there are pores with path that start on one side but never emerge; they are called "blind" pores. Also pores may emerge on the same side from which they started. Although pores can run straight, they are very likely to twist and turn in most materials, following tortuous paths that branch and interconnect. Pores may exhibit decreasing dimensions with depth or they may enlarge, giving rise to "bottle-neck" pores. To characterize pores mercury intrusion porosimeter produced by Micromeritics was used for quantifying the opening size, size range, area and volume of pores. When micronized the reaction product desirably has a porosity of about 30 to 80% with pore size diameter ranging from 0.001 $\mu$ to 100 $\mu$ with the maximum number of pores having an average diameter of about 1 $\mu$ (one micron).

Three samples of aluminum zirconium tetrachlorohydrex were prepared with glycerin levels of 4.64 wt %, 9.4 wt % and 16.6 wt % to determine the effect of glycerin level on pore area, pore diameter, % porosity, BET surface area and total intrusion volume. Chemical analysis of the samples and results of mercury intrusion porosimetry are shown in Table III.

Single point BET surface area was determined for various samples using Quantachrome Monsorb unit.

In order to determine the variation of surface area within a single sample, a sample of aluminum zirconium tetrachlorohydrex powder was micronized to the same specification as the numerous samples of this invention and was air classified into three fractions namely coarse (average particle size about 4 to 7 microns), fine fraction (average particle size about 1–4 micron) and superfine fraction (average particle size about 0.5 to 1.5 microns). The coarse fraction was about (62±9.4%) by weight, fine fraction was about (28±10%) by weight and superfine fraction was about (10±2.3) by weight. BET surface area measurement of the three fractions namely coarse, fine and superfine were (0.8–1.4 m$^2$/gm), (2.2 to 5.7 m$^2$/gm) and (11–13.6 m$^2$/gm) whereas the BET surface area of the composite sample was (2.8–3.3 m$^2$/gm). Computation of surface area of the composite sample based on fraction was in good agreement with the measurement value of the composite sample. All the BET surface area measurements were done using Quantachrome Monsorb Unit. The product of this invention could have a single point BET surface area from about 0.2 m$^2$/gm

TABLE III

| Example | % Al | % Zr | % Cl | % glycine | % glycerin* | partical size D50 | % <10$\mu$ | % <37$\mu$ | Total Intrusion Volume (mL/gm) | Total Pore Area (m2/gm) | Average Pore Diameter $\mu$ (micron) | % porosity |
|---|---|---|---|---|---|---|---|---|---|---|---|---|
| 12 | 13.5 | 13.4 | 17.2 | 11.3 | 4.64 | 2.4 | 94.6 | 100 | 0.7699 | 8.399 | 0.3667 | 59.88 |
| 13 | 13.1 | 13.4 | 16.6 | 10.4 | 9.4 | 2.0 | 100.0 | 100 | 0.8329 | 8.413 | 03960 | 60.98 |
| 14 | 11.9 | 12.6 | 15.1 | 10.4 | 16.6 | 1.8 | 96.8 | 100 | 0.9715 | 10.092 | 0.3850 | 63.77 |

*(glycerin as measured by analytical titration)

Mercury porosimetry results indicate that by increasing glycerin level from 4.5% to 9.4% there is a slight increase in porosity, pore diameter pore area and intrusion volume. Raising of glycerin level to 16.6% increased intrusion volume by 26% and pore area by 20%. In otherwords, with the increase in glycerin level the product appears to become more porous, however, the increase in porosity is small compared to the % increase in glycerin level.

A plot of log differential intrusion volume (ml/gm) vs pore size for the actives of examples 4, 5, 6, 7 showed that the pore size diameter for all the samples varied from 0.001 $\mu$ to 100 $\mu$ and the maximum number of pores seem to have an average diameter of 1 $\mu$. As the glycerin level is increased average pore diameter decreases and a plot of differential intrusion volume vs pore size showed a bimodal curve indicating pore intensity at about 1 $\mu$ and about 0.004 $\mu$.

For use in antiperspirant products, the product is either micronized or screened to achieve specific particle size distribution. Particles break into smaller particles when micronized with a range of sizes and shapes. Even though there is an inverse relationship between particle size and surface area, the ideal relationship is unlikely ever to be encountered. Thus, the actual exposed surface of particles is greater or sometimes very much greater than would be calculated assuming one geometric shape.

to about 14 m$^2$/gm. The BET surface area of unmicronized macrospherical product having average particle size of about 27.5 micron was 0.23 m$^2$/gm.

Since glycerin is a humectant, it is important to determine how the incorporation of glycerin affects equilibrium moisture (critical humidity) of the antiperspirant powder. (Equilibrium moisture was determined using the method described in a paper titled "Equilibrium Moisture Content of Antiperspirant Systems" published in Aerosol Age December 1974). Results of this study are shown in Table IV.

For aluminum zirconium tetrachlorohydrex glycine complex (Reach AZP-908, a product of Reheis Inc.) incorporation of 7.89% glycerin resulted in lowering the critical humidity from 18% to 10%. Further increase in glycerin level (7.89% to 19%) did not appear to lower critical humidity significantly.

To study the synergistic effect of urea and glycerin, a sample of antiperspirant powder was prepared in which about 8% of glycerin was replaced by 4.76% of glycerin and 4% of urea. This resulted in further lowering of the critical humidity to 8% showing synergistic effects between glycerin and urea. Lowering of the critical humidity is believed to enhance antiperspirancy; when compared on an equal active basis. The critical humidity should measure between about 6% to about 30% and the bulk density of the product preferably should be from about 0.15 gm/cc to about 1.3 gm/cc. Results of this study are shown in Table IV.

TABLE IV

| Example | % Al | % Zr | % Cl | % glycine | % glycerin* | % critical humidity |
|---|---|---|---|---|---|---|
| 15 | 14.03 | 13.94 | 17.6 | 6 | 4.76 + 4[b] | 8 |
| 16 | 13.5 | 12.77 | 16.6 | 9.3 | 7.89 | 10 |
| 17 | 11.82 | 11.4 | 14.9 | 9.7 | 19 | 10 |

[b] % urea

Examples 19, 20, 21 demonstrate that there is no significant increase in the amount of glycerin complexed when glycerin is mixed with ZHC glycinate solution at room temperature or at reflux temperature. The amount of glycerin complexed is less when glycerin is added to basic aluminum chloride at room temperature and mixed with refluxed ZHC glycinate solution.

TABLE V

| | | | | | | | % Glycerin | | | % Glycerin |
|---|---|---|---|---|---|---|---|---|---|---|
| Example | Process | % Al | % Zr | % Cl | % Glycine | Complexed | Free* | Total | Complexed |
| 18 | RE-301 mix/GL[a] at RT, mix/ZHC[b]-G (2 hrs reflux) | 15.0 | 13.2 | 17.5 | 11.4 | 0.68 | 1.86 | 2.54 | 26.77 |
| 19 | RE-301 mix/ZHC-GL-G (2 hrs reflux) | 14.1 | 13.2 | 17.4 | 11.4 | 1.49 | 1.05 | 2.54 | 58.66 |
| 20 | RE-301 mix/ZHC-GL-G (RT) | 14.5 | 13.5 | 17.5 | 10.8 | 1.61 | 0.93 | 2.54 | 63.38 |
| 21 | RE-301 mix/GL at RT, mix/ZHC-G(RT) | 14.2 | 13.4 | 17.3 | 11.2 | 1.67 | 0.87 | 2.54 | 65.75 |

[a] GL—glycerin
[b] G—glycine
*as measured by analytical titration

Examples in Table VI illustrates that there is no significant change in the amount of glycerin complexed when it is mixed with the basic aluminum chloride at room temperature or when it is refluxed with it from 2–4 hrs.

Also, the data from Table V and VI indicate that the quantity of glycerin that is complexed is a function of glycerin concentration and at what stage of the reaction process it is added.

TABLE VI

| | | | | | | Glycerin | | | % Glycerin |
|---|---|---|---|---|---|---|---|---|---|
| Example | Process | % Al | % Zr | % Cl | % Glycine | Complexed | Free* | Total | Complexed |
| 16 | RE-301 reflux GL[4], mix ZHC/G[2] | 13.5 | 12.77 | 16.6 | 9.3 | 2.36 | 7.89 | 10.25 | 23 |
| 22 | RE-301 mix/GL[1] (RT), mix/ZHC-G[2] | 11.87 | 12.78 | 16.22 | 11.3 | 2.72 | 8.68 | 11.4 | 23.86 |
| 23 | RE-301 reflux/GL[3] mix/ZHC-G[2] | 13.37 | 13.16 | 16.85 | 10.54 | 2.5 | 8.31 | 10.81 | 23.12 |

[1] RE-301 mixed with glycerin at RT.
[2] ZHC refluxed with glycine for 2 hrs.
[3] RE-301 refluxed with glycerin for 2 hrs.
[4] RE-301 refluxed with glycerin for 4 hrs.

Examples in Table VII demonstrate that activated or unactivated basic aluminum chlorides other than aluminum sesquichlorohydrate can be used successfully for making products of this invention.

TABLE VII

| Example | Process | % Al | % Zr | % Cl | % Glycine | % Free Glycerin* | Al/Zr | M/Cl |
|---|---|---|---|---|---|---|---|---|
| 24 | ACH reflux/GL[4], then mix/ZHC-G[2] | 14.1 | 14.1 | 16.2 | 10.23 | 7.4 | 3.45 | 1.48 |
| 25 | 15% activated ACH reflux/GL then mix/ZHC-G[2] | 17.28 | 9.49 | 14.96 | 10.44 | 4.06 | 6.27 | 1.76 |

*(as measured by analytical titration)

EXAMPLE 26

In order to improve flow properties and skin feel of the novel antiperspirant product of this invention, it was codried with silicon oil (B-118F) supplied by Siltech at 1.0% by wt. (see example 26 in Table VIII). the resultant spray dried powder had an average particle size of 8.6 μ was spherical in shape and exhibited improved flow properties.

To further demonstrate that glycerin can be added at any stage of the process, example 26 was carried out as follows:

EXAMPLES 27 and 28

1116 gm of RE 301 solution (12.1% Al, 9.24% Cl) was mixed with 720 g ZHC glycinate (18.39% Zr, 8.74% Cl, 17.36% glycine refluxed for 2 hours and cooled at room temperature). 110 g glycerin was added to the above solution and mixed at room temperature until homogeneous. The resultant solution was spray dried. The powder was micronized and analyzed. Example 28 was prepared in the pilot plant using the same procedure as example 26. Anayltical results are shown in Table VIII.

TABLE VIII

| Example | % Al | % Zr | % Cl | % Glycine | % Glycerin | Al/Zr | M/Cl |
|---|---|---|---|---|---|---|---|
| 26 | 13.5 | 12.66 | 16.75 | 10.1 | 7.81 | 3.67 | 1.35 |
| 27 | 12.84 | 12.61 | 16.54 | 12.3 | 8.7 | 3.51 | 1.31 |
| 28 | 13.3 | 13 | 16.1 | 11.9 | 7.8 | 3.52 | 1.39 |

Measurement of overall surface energies of the micronized powders of this invention indicated that surface energy could vary from 30 to 60 mg/m².

In order to study the effect of the novel antiperspirant of this invention on the finished formulation. "Reduced Residue Antiperspirant" sticks were prepared using the following formulation.

EXAMPLE 29

Enhanced efficacy aluminum zirconium tetrachlorohydrex glycine (Reach AZP-908 Super Ultrafine) powder, a product of Reheis Inc., was used as a control to compare with the novel antiperspirant of this invention. In the control experiment equivalent amount of glycerin was added during the formulation phase.

Antiperspirant Stick Formula & Procedure

| Ingredients | | % By Wt. % |
|---|---|---|
| A. | Aluminum Zirconium Tetrachlorohydrex (Reach AZP-908 SUF, a product of Reheis Inc.) (a) | 24.0 |
| B. | Cyclomethicone (pentamer) | 32.5 |
| C. | Polydecene (b) | 9.0 |
| D. | PPG-14 Butyl Ether (c) | 9.0 |
| E. | Hydrogenated Castor Oil | 2.5 |
| F. | PEG-8 Distearate (d) | 1.0 |
| G. | Stearyl Alcohol | 18.0 |
| H. | Talc 5251L (e) | 3.0 |
| I. | Cab-O-Sil M-5 (f) | 0.5 |
| J. | Fragrance | 0.5 |
| | | 100.0 |

Procedure

1) Combine C, D, E, F and G with mixing and heat to 85° C. or until clear. Cool to 70° C.
2) Separately heat B to 70° C.
3) Add Step 2 to Step 1 and mix well.
4) Slowly add I, H, and A while maintaining 70° C. Mix well until homogeneous.
5) Cool to 56–58° C. and add J. Mix well.
6) Pour into stick containers.
(a) Reheis Inc.
(b) Lipo Chemical (Silkflo 364 NF)
(c) Amerchol Corp. (Fluid AP)
(d) Protameen (Protamate 400 DS)
(e) Whittaker, Clark, & Daniels
(f) Cabot Corp.

Chemical analysis of the two active ingredients used are shown in Table IX.

TABLE IX

| | % Al | % Zr | % Cl | % Glycine | % Glycerin | Al/Zr | M/Cl |
|---|---|---|---|---|---|---|---|
| Reach AZP-908 | 14.8 | 13.9 | 17.8 | 11.7 | 0 | 3.67 | 1.39 |
| Novel AP product | 14.1 | 12.8 | 17.2 | 10.8 | 8.2 | 3.79 | 1.36 |

Table X summarizes the exact quantity of ingredients used to make antiperspirant sticks.

TABLE X

| | Ingredients | B | C | D | E | F |
|---|---|---|---|---|---|---|
| A | AP powder | 168* | 179+ | 179+ | 179+ | 168* |
| B | Cyclomethicone | 213.5 | 216.5 | 220 | 241 | 252 |
| C | Polydecene | 63 | 63 | 63 | 63 | 63 |
| D | PPG-14 butyl ether | 63 | 63 | 63 | 63 | 63 |

TABLE X-continued

| | Ingredients | B | C | D | E | F |
|---|---|---|---|---|---|---|
| E | Hydrogenated castor oil | 17.5 | 17.5 | 17.6 | 17.5 | 17.5 |
| F | PEG-8 distearate | 7.0 | 7.0 | 7.0 | 7.0 | 7.0 |
| G | Stearyl alcohol | 126 | 126 | 126 | 126 | 126 |
| H | Talc 5251L | 21 | 21 | 21 | — | — |
| I | Cab-O-Sil-MS | 3.5 | 3.5 | — | — | — |
| J | Fragrance | 3.5 | 3.5 | 3.5 | 3.5 | 3.5 |
| K | Glycerin | 14 | — | — | — | — |

*Reach AZP-908 SUF
+Novel active of this invention

Sticks were evaluated for: uniformity of active by analysis of %Zr in top, middle and bottom sections of sticks; appearance (color); and hardness at intervals of 1 day and 1 month after application on forearm (for white residue and tackiness) by an expert formulator i.e. by a Ph.D. chemist with 30+years experience in formulation. Results are listed in Table XI.

TABLE XI

| Designation | B | C | D | E | F |
|---|---|---|---|---|---|
| Active & concentration on an anhydrous basis | Reach AZP-908 | Novel active of this invention | Novel active of this invention | Novel active of this invention | Novel active of this invention |
| Color ΔYB | 8.7 | 6.35 | 6.39 | 7.9 | 14.21 |
| ΔRG | 1.92 | 1.39 | 1.42 | 1.85 | 4.06 |
| Hardness 1 day | 3.1 | 3 | 3.9 | 3.9 | 3.7 |
| 1 month | 2 | 3.2 | 4.1 | 4.4 | 4.0 |
| Active Distribution | | | | | |
| % Zr Top | 3.37 | 3.45 | 3.34 | 3.42 | 3.55 |
| Middle | 3.40 | 3.31 | 3.30 | 3.37 | 3.35 |
| Bottom | 3.42 | 3.43 | 3.35 | 3.34 | 3.48 |
| Application | Sandy Unacceptable | Goes on smooth | Goes on smooth | Goes on smooth | Goes on smooth |
| Tackiness | Very slightly tacky | Very slightly tacky | Very slightly tacky | Very slightly tacky | Non-tacky |
| White Residue | | | | | |
| 15 minutes | Mod. White | Very slight residue | Very slight residue | Very slight residue | Very slight residue |
| 30 minutes | Mod. White | Very slight residue | Very slight residue | Very slight residue | No white residue |

Results of Table X indicate that antiperspirant sticks made from the novel antiperspirant salt of this invention exhibited better appearance had no grittiness, and left very slight residue. Comparison with stick B where glycerin was added during the formulation showed more white residue. Stick E appeared to be somewhat softer (hardness of 4.4 as opposed to 2.0 for control). However, average hardness of most commercial sticks is in the range of 4±0.5. Besides its excellent moisturizing and plasticizing properties, the novel antiperspirant allows one to eliminate the use of silica and talc, both of which present safety and health related issues. Color measurement as indicated by ΔYB (yellow) and ΔRG (reddish green) indicate that product with glycerin is whiter.

Formulated product with the novel antiperspirant product of this invention was more viscous and "creamier" at 60° C. before filling into containers. Viscosity of the formulated novel antiperspirant product was lower than the conventional product indicating that pour temperature could be lowered. This property represents an additional savings in processing of this product.

The present invention may be embodied in other specific forms without departing from the spirit of essential attributes thereof and, accordingly, reference should be made to the appended claims, rather than to the foregoing specifications as indicating the scope of the invention.

What is claimed is:

1. A skin friendly antiperspirant composition which comprises from about 70% to about 98% by weight of an antiperspirant active selected from those aluminum-zirconium-glycine salts having the formula:

$$Al_n Zr(OH)_{(3n+4-x)} Y_x (AA) q(R) p \quad (I)$$

wherein "n" is from 2.0 to 10.0;
wherein "x" is from 1.4 to 12.3, calculated from metal to anion ratio of from 0.9:1 to 2.1:1;
wherein "Y" is Cl, Br, I and/or $NO_3$
wherein "q" is from 0.5 to 3.0; AA is amino acid, and wherein "R" is an organic solvent having at least two carbon atoms and at least one hydroxy group and "p" has a value of from zero to 1.5;
and those basic aluminum chlorides with the formula:

$$Al_2(OH)_{6-x1} Y_{x1} (R) p \quad (II)$$

wherein Y is Cl, Br, I and/or $NO_3$ and $x_1$ is greater than zero and less than or equal to six (i.e., $0 < x1 \leq 6$); and wherein "R" is an organic solvent having at least two carbon atoms and at least one hydroxy group and "p" has a value of from zero to 1.5;

(III) and those aluminum and aluminum-zirconium salts combined with zinc and/or tin and from about 2% to about 30% by weight of a polyhydric alcohol having at least three to about 12 carbon atoms and at least three hydroxy groups and wherein from about 2% to about 70% of the polyhydric alcohol is complexed with the metal or metals present in the antiperspirant salts.

2. The antiperspirant powder composition of claim 1 which when micronized, has a porosity of about 30 to 80% with pore size diameter ranging from 0.001 μ to 100 μ with the maximum number of pores having an average diameter of about 1 μ (one micron).

3. The antiperspirant composition of claim 1 having single point BET surface area from 0.2 m²/gm to 14 m²/gm.

4. The antiperspirant composition of claim 1 characterized in having a critical humidity from about 6% to 30%.

5. The antiperspirant of composition claim 1 characterized in that it has a bulk density from about 0.15 gm/cc to about 1.3 gm/cc.

6. The antiperspirant composition of claim 1 characterized in that it has a surface energy of 30 mg/m² to 60 mg/m².

7. The antiperspirant composition of claim 2 having a single point BET surface area from 0.2 m²/gm to 14 m²/gm.

8. The antiperspirant composition of claim 7 characterized in that it has a critical humidity of from about 6% to about 30% and a bulk density of from about 0.15 gm/cc to about 1.3 gm/cc.

9. The antiperspirant composition of claim 8 characterized in that it has a surface energy from about 30 mg/m² to about 60 mg/m².

10. The antiperspirant composition of claim 1 wherein the antiperspirant active is selected from those of formula (I) and the polyhydric alcohol is selected from glycerin, diglycerol and mixtures thereof.

11. The antiperspirant composition of claim 1 wherein the antiperspirant active is selected from those of formula (I) and the polyhydric alcohol comprised a blend of glycerin and urea.

12. The antiperspirant composition of claim 9 wherein the polyhydric alcohol is glycerin.

13. The antiperspirant composition of claim 1 wherein the antiperspirant active is that of formula II.

14. The antiperspirant of claim 12 wherein the polyhydric alcohol is selected from glycerin, diglycerol and mixtures thereof.

15. The antiperspirant composition of claim 1 wherein the antiperspirant active is selected from those of formula II and the polyhydric alcohol comprises a blend of glycerin and urea.

16. The antiperspirant composition of claim 1 of wherein the polyhydric alcohol is a mixture of glycerin and glyceridacid.

17. The antiperspirant composition of claim 1 wherein the polyhydric alcohol is glycerin in combination with α hydroxy acids selected from tartaric acid, malic acid, 2 hydroxy octanoic acid, 2 hydroxy decanoic acid, salicylic acid.

18. The antiperspirant composition of claim 1 wherein the antiperspirant active is selected from an aluminum/zinc complex and an aluminum/zirconium/zinc complex.

19. The antiperspirant composition of claim 1 including a surface/flow property modifier.

20. The antiperspirant of claim 19 in which the surface/flow property modifier is a silicone oil.

21. The antiperspirant composition of claim 10 wherein the polyhydric alcohol is glycerin, wherein the BET surface is about 2–4 m²/gm, the surface energy is about 40–55 mg/m² the bulk density is about 0.5–0.8 gm/cc the average particle size is about 85–95% through 10 micron, and critical himidity is about 8–12%.

22. A method of preparing skin-friendly antiperspirant composition of from about 70% to about 98% by weight of an antiperspirant active and from about 2% to about 30% by weight of a polyhydric alcohol having at least 3 carbon atoms and at least 3 hydroxy groups and wherein from about 2% to about 70% of the polyhydric alcohol is complexed with the antiperspirant active comprises:

mixing a basic aluminum salt having the general formula:

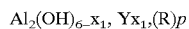

$Al_2(OH)_{6-x_1},Yx_1,(R)p$ wherein Y is selected from Cl, Br, I and NO₃;
x₁ is greater than zero and less than or equal to six;
R is a polyhydric alcohol having at least 2 carbon atoms and at least one hydroxy group; and
p has a value with from about zero to about 1.5;

with a polyhydric alcohol having at least three carbon atoms arid at least three hydroxy groups;

at a temperature ranging from room temperature to about 105° C.;

cooling the reaction mixture to room temperature;

mixing the cooled reaction mixture with a zirconium hydroxy chloride glycinate solution having a chloride to zirconium ratio of from about 2:1 to about 0.8:1 and which has been mixed at a temperature of from room temperature to about reflux temperature with a reactant selected from amino acids and mixtures thereof; and cooling the reaction mixture to room temperature.

23. The method of claim 22 wherein the reaction mixture is dried.

24. The method of claim 22 wherein Y of the general formula is chloride.

25. The method of claim 22 wherein the amino acid reactant is glycine.

26. The method of claim 22 wherein the polyhydric alcohol is added to the zirconium hydroxy chloride glycinate solution during the refluxing of the reaction mixture.

27. The method of claim 22 wherein the polyhyroxy alcohol is added to the zirconium hydroxy chloride glycinate solution before refluxing.

28. The method of claim 22 wherein the polyhydric alcohol is added to the zirconium hydroxy chloride glycinate solution after the refluxing and wherein the reaction product is spray dried.

29. The method of claim 22 wherein the polyhydric alcohol is glycerin.

30. The method of claim 29 wherein a portion of the glycerin is added to the basic aluminum salt and the remainder of the glycerin is added to the zirconium hydroxy chloride glycinate.

31. The method of claim 22 wherein a zinc compound is added to the aluminum-zirconium salt.

32. The method of claim 23 wherein the drying of the reaction product is by spray drying.

33. The method of claim 22 wherein an additive is included that improves the flow properties and modifies the surface energy of the antiperspirant product.

34. The method of claim 23 wherein drying is by a means selected from oven drying, freeze drying, tray drying and vacuum drying.

35. The method of claim 23 wherein the dried product is micronized to obtain the desired particle size and surface area.

36. The method of claim 22 further comprising screening the dried powder using a centrisifter or vibratory screen or an alpine screen.

\* \* \* \* \*